(12) United States Patent
Bonnet et al.

(10) Patent No.: US 11,555,003 B2
(45) Date of Patent: Jan. 17, 2023

(54) BIOSOURCED VINYLIDENE DIFLUORIDE MONOMER AND POLYMERS CONTAINING IT

(71) Applicant: Arkema France, Colombes (FR)

(72) Inventors: Anthony Bonnet, Colombes (FR); Jean-Luc Dubois, Colombes (FR)

(73) Assignee: Arkema France, Colombes (FR)

( * ) Notice: Subject to any disclaimer, the term of this patent is extended or adjusted under 35 U.S.C. 154(b) by 230 days.

(21) Appl. No.: 17/055,311

(22) PCT Filed: Jun. 12, 2019

(86) PCT No.: PCT/FR2019/051418
§ 371 (c)(1),
(2) Date: Jan. 6, 2021

(87) PCT Pub. No.: WO2019/239065
PCT Pub. Date: Dec. 19, 2019

(65) Prior Publication Data
US 2021/0147325 A1    May 20, 2021

(30) Foreign Application Priority Data

Jun. 15, 2018 (FR) ..................... 1855278

(51) Int. Cl.
| | | |
|---|---|---|
| *C07C 21/18* | (2006.01) | |
| *C07C 17/06* | (2006.01) | |
| *C07C 17/04* | (2006.01) | |
| *C07C 17/087* | (2006.01) | |
| *C07C 17/20* | (2006.01) | |
| *C07C 17/25* | (2006.01) | |
| *C08F 14/22* | (2006.01) | |

(52) U.S. Cl.
CPC .............. *C07C 21/18* (2013.01); *C07C 17/04* (2013.01); *C07C 17/06* (2013.01); *C07C 17/087* (2013.01); *C07C 17/206* (2013.01); *C07C 17/25* (2013.01); *C08F 14/22* (2013.01)

(58) Field of Classification Search
None
See application file for complete search history.

(56) References Cited

U.S. PATENT DOCUMENTS

| | | | |
|---|---|---|---|
| 2,322,258 A | 6/1943 | Strosacker et al. | |
| 3,245,041 A | 4/1966 | Levinthal et al. | |
| 2009/0187052 A1 | 7/2009 | Strebelle et al. | |
| 2011/0251443 A1 | 10/2011 | Dubois | |

FOREIGN PATENT DOCUMENTS

| | | |
|---|---|---|
| CN | 107216234 A | 9/2017 |
| JP | 4739086 B2 | 8/2011 |

OTHER PUBLICATIONS

Ruzicka, J. A. et al. "Synthesis of [1-14C]-2,2-Difluoroethene from [14C]-Formaldehyde" Journal of Labelled Compounds and Radiopharmaceutica/s-Vo/. XXX/V, No. 1, 1994, pp. 59-65 (Year: 1994).*

* cited by examiner

*Primary Examiner* — Medhanit W Bahta
(74) *Attorney, Agent, or Firm* — Joanne Rossi

(57) ABSTRACT

The invention relates to biosourced vinylidene difluoride. The invention also relates to methods for preparation of biosourced vinylidene difluoride from various renewable raw materials. The invention also relates to homopolymers of vinylidene difluoride obtained from polymerization of said monomer, and also copolymers obtained by copolymerization of said monomer with one or several compatible comonomers. Finally, the invention relates to the use of said homopolymers or copolymers in applications, such as chemical engineering or electronics, in particular mass-market electronic devices.

14 Claims, No Drawings

BIOSOURCED VINYLIDENE DIFLUORIDE MONOMER AND POLYMERS CONTAINING IT

This application is a national stage application under 35 U.S.C. § 371 of PCT Application PCT/FR2019/051418, filed Jun. 12, 2019; which claims benefit to French National Patent Number 1855278, filed Jun. 15, 2018; said applications are incorporated herein by reference.

FIELD OF THE INVENTION

The object of the present invention is a biosourced vinylidene difluoride. The invention also relates to methods for preparation of biosourced vinylidene difluoride from various renewable raw materials. The invention also relates to homopolymers of vinylidene difluoride obtained from polymerization of said monomer, and also copolymers obtained by copolymerization of said monomer with one or several compatible comonomers. Finally, the invention relates to the use of said homopolymers or copolymers in any application where the appearance of these polymers is essential and/or their properties depend on their degree of purity; it involves applications in the automotive industry, fluid filtration, in particular water, offshore, medical, potable water transport, semiconductor market, cabling, lithium ion batteries, photovoltaics, sports items and sports textiles. Preferred applications are chemical engineering and electronics, especially mass market electronic devices.

STATE-OF-THE-ART

Vinylidene difluoride (1,1-difluoroethylene, or VDF) is a colorless, odorless and non-toxic gas. This fluoridated olefin has the advantage of not containing chlorine or bromine and consequently the toxicity thereof is less compared to chlorotrifluoroethylene (CTFE) or bromotrifluoromethylene (BrTFE). Further, it is not explosive like tetrafluroethylene (TFE) and it is less costly than TFE, hexafluoropropane (HFP), CTFE or BrTFE.

VDF is well known for its use as monomer in the production of poly(vinylidene difluoride), PVDF, and as co-monomer in the production of various types of fluoridated polymers.

Conventional VDF is obtained by vapor phase cracking or catalytic cracking of petroleum fragments. It is synthesized industrially by pyrolytic dehydrochlorination of 1-chloro-1,1-difluoromethane according to the reaction:

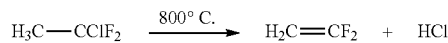

The precursor 1-chloro-1,1-difluoroethane can be prepared according to four pathways:

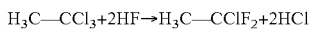

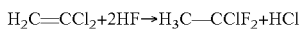

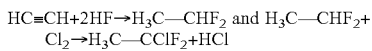

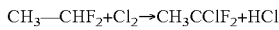

Other synthetic pathways for VDF are known.
dehydrobromination of 1-bromo-1,1-difluoroethane;
dehydrofluoridation of 1,1,1-trifluoroethane;
dechlorination of 1,2-dichloro-1,1-difluoroethane;
dehydrogenation/oxydehydrogenation of 1,1-difluoroethane.

Under hydrofluorination 1,1,2-trichloroethylene yields 1,2-dichloro-1,1-difluoroethane, which itself can yield difluoroethylene by hydrogenolysis.

The raw materials used in these various methods for synthesizing VDF are mainly of fossil or petroleum origin. These production methods thus contribute to increasing the greenhouse effect and are considered pollutants to the environment. Further, global reserves of raw materials of fossil origin (petroleum and natural gas) continue to decline, making the search for new usable sources of raw materials, which are renewable, imperative. Finally, it was observed that fluoridated polymers made from conventional VDF had undesirable properties; in particular they can contain impurities that increase the yellowing index (YI), a matter of particular concern for applications like chemical engineering or even mass-market electronic devices, where esthetics and coloration consistency are required.

There is therefore a need to have a vinylidene difluoride prepared from renewable sources that is free of any impurity that could affect the properties of the polymer prepared from this monomer, such as thermal aging properties or the yellowing index.

With this new biosourced monomer, fluoridated polymers can be produced which combine several advantages, specifically combining technical and environmental performance. Therefore the object of the present invention is to conceive of new VDF based fluoridated polymers which are of renewable origin and whose performance is at least equivalent to that of fluoridated polymers of fossil origin.

DESCRIPTION OF THE INVENTION

First, the invention relates to biosourced vinylidene difluoride. Characteristically, the renewable carbon concentration of biosourced VDF is at least 1% by atom, as determined by the $^{14}C$ concentration according to the NF EN 16640 standard of Apr. 15, 2017. This corresponds to a $^{14}C/^{12}C$ isotopic ratio in the VDF molecule of at least $1.2 \times 10^{-14}$.

According to an embodiment, the renewable carbon concentration in the biosourced VDF is greater than 5%, preferably greater than 10%, preferably greater than 25%, preferably greater than or equal to 33%, preferably greater than 50%, preferably greater than or equal to 66%, preferably greater than 75% preferably greater than 90%, preferably greater than 95%, preferably greater than 98%, preferably greater than 99% and advantageously equal to 100%.

Another object of the invention is a method for preparation of the compound according to the invention, comprising the step of providing biosourced ethylene having a renewable carbon concentration of at least 1%, and the transformation into biosourced vinylidene difluoride by multistep synthesis. The first step of synthesis is the production of vinyl chloride from this biosourced ethylene. Several synthetic pathways are then possible.

According to an embodiment, the biosourced vinyl chloride is transformed into biosourced VDF via the following synthetic intermediates: 1,1,2-trichloroethane, 1,1,1-trichloroethane and 1-chloro-1,1-difluoroethane.

According to an embodiment, the biosourced vinyl chloride is transformed into biosourced VDF via the following synthetic intermediates: 1,1,2-trichloroethane, 1,1-dichloroethane and 1-chloro-1,1-difluoroethane.

According to an embodiment, the biosourced vinyl chloride is transformed into biosourced VDF via the following synthetic intermediates: 1,1-dichloroethane, 1,1,1-trichloroethane and 1-chloro-1,1-difluoroethane.

Another object of the invention is a biosourced vinylidene difluoride homopolymer (PVDF) prepared by polymerization of said biosourced monomer.

The invention also relates to biosourced fluoridated copolymers obtained by copolymerization of said biosourced monomer with one or more compatible comonomers.

The object of the present invention is also the use of biosourced PVDF and biosourced fluoridated copolymers conforming to those previously defined in various applications, such as chemical engineering or electronics, in particular mass-market electronic devices: audio and video equipment for domestic and commercial use, electronic games and entertainment equipment, bowling and billiard equipment, cable and satellite communication equipment, electronic components used in audio and video equipment, closed-circuit TV equipment and musical instruments. Generally, biosourced fluoridated polymers according to the invention are used in any application where the appearance of these polymers is essential and/or their properties depend on their degree of purity; it involves applications in the automotive industry, fluid filtration, in particular water, offshore, medical, potable water transport, semiconductor market, cabling, lithium ion batteries, photovoltaics, sports items and sports textiles.

Advantageously, the biosourced PVDF and/or the biosourced fluoridated copolymers from the invention are used alone or in mixture with other polymers, where said biosourced fluoridated polymers represent from 5 to 100%, preferably from 5 to 70%, and preferably from 5 to 30% by mass.

The disadvantages from the state-of-the-art can be overcome with the present invention. More specifically it provides biosourced vinylidene difluoride made from biosourced raw materials thus meeting sustainable development requirements. It is particularly appropriate for production of fluoridated polymers for applications requiring consistent, high purity properties. Thus, the end use of the biosourced fluoridated polymers is not limited to simply replacing fluoridated polymers of fossil origin, but to provide high performance biosourced products as well.

DESCRIPTION OF EMBODIMENTS OF THE INVENTION

The invention is now described in more detail and without limitation in the following description.

According to a first aspect, the invention relates to the vinylidene difluoride compound characterized in that it has a renewable carbon content of at least 1% by atom.

Carbon from a biomaterial comes from plant photosynthesis and therefore from atmospheric $CO_2$. The breakdown (breakdown is also understood to mean the end-of-life combustion/incineration) of these materials into $CO_2$ therefore does not contribute to warming because there is no increase of carbon emitted into the atmosphere. The $CO_2$ balance from biomaterials is therefore clearly better and contributes to reducing the carbon footprint of the resulting products (only the production energy needs to be considered). In contrast, a material of fossil origin breaking down into $CO_2$ is going to contribute to the increase of the $CO_2$ level and thereby to global warming.

The compounds according to the invention will therefore have a carbon footprint which will be better than those from compounds obtained from a fossil source.

The invention therefore improves the ecological balance during production of vinylidene difluoride monomers and of fluoridated polymers prepared from these monomers.

The term "renewable carbon" indicates that the carbon has a natural origin and comes from a biomaterial (or biomass), as indicated below.

The term "biosourced" means "coming from biomass."

A material of renewable origin, also called biomaterial, is an organic material in which the carbon comes from $CO_2$ recently fixed (on the human scale) from the atmosphere by photosynthesis. On earth, this $CO_2$ is captured or fixed by plants. At sea, $CO_2$ is captured or fixed by photosynthetic bacteria or plankton. A biomaterial (100% natural origin carbon) has a $^{14}C/^{12}C$ isotopic ratio over $10^{-12}$, typically on the order of $1.2 \times 10^{-12}$, whereas the fossil material has a zero ratio. In fact the $^{14}C$ isotope is formed in the atmosphere and is then incorporated by photosynthesis over a time scale of several decades at most. The half-life of $^{14}C$ is 5730 years. Therefore, the materials coming from photosynthesis, specifically plants in general, have of necessity a minimum concentration of $^{14}C$ isotope.

Biomass is therefore any material of biological origin, excluding materials buried in geological formations and/or fossilized materials. Examples of biomass are plants, trees, algae, marine organisms, microorganisms, animals, etc. (all or part of these organisms). Renewable materials are composed of biomass and can be continuously reconstituted.

The biomaterial concentration or renewable carbon concentration is determined by application of the NF EN 16640 standard whose subject matter is Bio-based products—Determination of the bio-based carbon content of products using the radiocarbon method.

This European Standard describes a method with which to determine the biosourced carbon concentration in products based on measuring the $^{14}C$ concentration. It also specifies two test methods to be used for determining the 14C concentration, based on which the concentration of biosourced carbon is calculated:

Method A: liquid scintillation counter (LSC);
Method B: accelerator mass spectrometry (AMS).
A third method—Method C: beta ionization (BI)—can also be used for determining the $^{14}C$ concentration.

The biosourced carbon concentration is expressed as a fraction of sample mass or fraction of the total carbon concentration.

The test and analysis methods specified in the European Standard EN 16640:2017 are compatible with the methods described in ASTM D 6866-12.

In the vinylidene difluoride molecule according to the invention, the $^{14}C/^{12}C$ isotopic ratio is at least $1.2 \times 10^{-14}$.

According to a second aspect, the object of the invention is a method for preparation of the compound according to the invention, using products of natural origin as starting products for production of vinylidene difluoride.

According to an embodiment, the starting product is ethylene obtained from ethanol produced directly from biomass. An easily hydrolyzable carbohydrate biomass (such as grains, beets) is fermented using a yeast (for example *Saccharomyces cerevisiae*) or bacteria (for example, *Zyomonas* or *Clostridium*). Ethanol can be produced from a ligno-cellulose biomass (e.g. wood, sugarcane, straw) by another route. Such methods are known to the person skilled in the art. For example, they comprise the fermentation of vegetable matter in the presence of one or more yeasts, followed by a distillation with which to recover the ethanol in more concentrated aqueous solution which is finally treated in order to further increase the molar concentration of ethanol. The ethanol resulting from fermentation is then dehydrated in a first reactor in a mixture of ethylene and water. Preferably, the alcohol is injected into the first reactor head. This dehydration step is generally done in the presence of a catalyst which can in particular be based on γ-alumina. As an example, it was shown that a volumetric flow rate ratio of liquid ethanol to the catalyst volume of 1 hr$^{-1}$ and an average catalytic bed temperature of 400° C. led to a nearly complete conversion of ethanol with an ethylene selectivity of about 98% mol. Dehydration can also be carried out in the presence of steam, which then also serves as the heat carrying fluid compensating for the consumption of heat by the dehydration reaction, which is endothermic.

The method according to the invention comprises a step for the supply of biosourced ethylene having a renewable carbon content of at least 1 atomic % and the transformation into biosourced vinylidene difluoride by multistep synthesis. The first step of synthesis is the production of vinyl chloride monomer (VCM) from this biosourced ethylene. VCM is synthesized by oxychlorination of ethylene in the presence of oxygen and HCl, or by direct chlorination of ethylene in the presence of dichloride ($Cl_2$) followed by distillation and cracking at 500° C. followed by a new distillation in order to separate the dichloroethane from the vinyl chloride. A detailed description of the method for synthesis of VC is found in Techniques de l'Ingénieur—references J6250V1 (Jun. 10, 1993), and J6020-J1143V1 (Sep. 10, 1984). VCM can also be produced by hydrochlorination of acetylene, as indicated below.

Several synthetic pathways are then possible.

According to an embodiment, the biosourced vinyl chloride is transformed into biosourced VDF via the following synthetic intermediates: 1,1,2-trichloroethane, 1,1,1-trichloroethane and 1-chloro-1,1-difluoroethane.

The reaction steps are indicated below:

Production of biosourced T112 (1,1,2-trichloroethane or $CH_2Cl$—$CHCl_2$) by cold chlorination ($Cl_2$) from biosourced VCM:

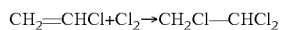

Production of biosourced T111 (1,1,1-trichloroethane or $CCl_3$—$CH_3$) from the biosourced T112 by reaction with HCl gas, for example, going through $CH_2$=$CCl_2$ (CV2) according to different variants by dehydrochlorination with sodium hydroxide or calcium hydroxide, then hydrochlorination of CV2 into T111:

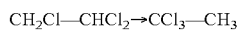

Production of biosourced 142 b (1,1,1-chlorodifluoroethane or $CH_3$—$CF_2Cl$) from biosourced T111 and reaction with HF:

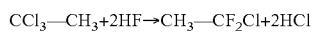

Production of biosourced vinylidene difluoride (VDF or $CF_2$=$CH_2$) from biosourced 142 b by thermal dehydrochlorination:

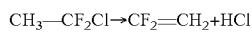

According to an embodiment, the biosourced vinyl chloride is transformed into biosourced VDF via the following synthetic intermediates: 1,1,2-trichloroethane, 1,1-dichloroethane and 1-chloro-1,1-difluoroethane.

The reaction steps are indicated below:
Production of biosourced T112 (1,1,2-trichloroethane or $CH_2Cl$—$CHCl_2$) by cold chlorination ($Cl_2$) from biosourced VCM:

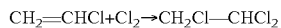

Production of biosourced CV2 (1,1-dichloroethene or $CH_2$=$CCl_2$) from biosourced T112 by dehydrochlorination by NaOH (or calcium hydroxide) with production of brine:

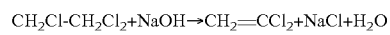

Production of biosourced 142 b (1,1,1-chlorodifluoroethane or $CH_3$—$CF_2Cl$) from biosourced CV2 by fluoridation:

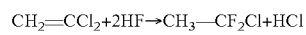

Production of biosourced vinylidene difluoride (VDF or $CF_2$=$CH_2$) from biosourced 142 b by thermal dehydrochlorination:

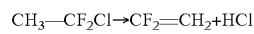

According to an embodiment, the biosourced vinyl chloride is transformed into biosourced VDF via the following synthetic intermediates: 1,1-dichloroethane, 1,1,1-trichloroethane and 1-chloro-1,1-difluoroethane.

The reaction steps are indicated below:
Production of biosourced D11 (1,1-dichloroethane or $CHCl_2$—$CH_3$) from biosourced VCM by hydrochlorination:

$CH_2$=$CHCl$+$HCl$→$CHCl_2$—$CH_3$

Production of biosourced T111 (1,1,1-trichloroethane or $CCl_3$—$CH_3$) from biosourced D11 by chlorination:

$CHCl_2$—$CH_3$+$Cl_2$→$CCl_3$—$CH_3$+$HCl$

Production of biosourced 142 b (1,1,1-chlorodifluoroethane or $CH_3$—$CF_2Cl$) from biosourced T111 and reaction with HF:

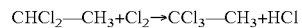

Production of biosourced vinylidene difluoride (VDF or $CF_2$=$CH_2$) from biosourced 142 b by thermal dehydrochlorination:

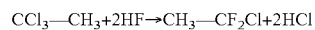

Each of these three pathways can be used by starting with the reaction of biosourced acetylene with hydrochloric acid for making biosourced CVM. Biosourced acetylene is produced from biogas containing methane and/or from calcium carbide having itself been prepared from a renewable carbon source (e.g. wood charcoal, lignin or other). Such a method starting from acetylene is described in Techniques de l'Ingénieur, reference J6250 and also in document FR 2,939, 132.

Another object of the invention is a biosourced vinylidene difluoride homopolymer (PVDF) comprising biosourced vinylidene fluoride units. Homopolymerization of VDF is generally done by methods such as suspension or emulsion. Just the same, synthesis of PVDF can be done in solution or in bulk.

The VDF homopolymer according to the invention comprises VDF monomers coming from renewable resources, potentially from monomers coming from fossil resources. When the PVDF is synthesized from a mixture of monomers (biosourced and fossil origin), at least 20% by weight of the mixture is represented by biosourced monomer units.

Advantageously, the PVDF homopolymer only comprises VDF units of renewable origin determined according to the EN 16640:2017 standard.

The invention also relates to biosourced fluoridated copolymers comprising biosourced vinylidene difluoride units and one or more types of comonomer units compatible with vinylidene difluoride. These monomers can be halogenated (e.g. fluoridated, chlorinated or brominated) or non-halogenated.

The following are some examples of appropriate fluoridated comonomers: vinylfluoride (VF), tetrafluoroethylene (TFE), hexafluoropropylene (HFP), trifluoropropenes and in particular 3,3,3-trifluoropropene, tetrafluoropropenes and in particular 2,3,3,3-tetrafluoropropene or 1,3,3,3-tetrafluoropropene, hexafluoroisobutylene, perfluorobutylethylene, pentafluoropropenes and in particular 1,1,3,3,3-pentafluoropropene or 1,2,3,3,3-pentafluoropropene, perfluoroalkylvinylethers and in particular those with general formula Rf—O—CF—CF$_2$, where Rf is an alkyl group, preferably in C1 to C4 (preferred examples being perfluoropropylvinylether or PPVE and perfluoromethylvinylether or PMVE). The fluoridated monomer can comprise a chlorine or bromine atom. In particular, it can be chosen among bromotrifluoroethylene, chlorofluoroethylene, chlorotrifluoroethylene and chlorotrifluoropropene. Chlorofluoroethylene can designate either 1-chloro-1-fluoroethylene, or 1-chloro-2-fluoroethylene. The isomer 1-chloro-1-fluoroethylene is preferred. Chlorotrifluoropropene is preferably 1-chloro-3,3,3-trifluoropropene or 2-chloro-3,3,3-trifluoropropene.

The biosourced fluoridated copolymer can also comprise non-halogenated monomers such as ethylene, in particular biosourced ethylene, and/or acrylic or methacrylic comonomers.

The object of the present invention is also the use of biosourced PVDF and biosourced fluoridated copolymers consistent with those previously defined in various applications where the appearance of these polymers is essential and/or their properties depend on their degree of purity; it involves applications in chemical engineering, automotive, fluid filtration, in particular potable water, offshore, medical, potable water transport, semiconductor market, cabling, lithium ion batteries, photovoltaics, sports items and sports textiles.

Preferred applications are in electronics, in particular for production of mass-market electronic devices: audio and video equipment for domestic and commercial use, electronic games and entertainment equipment, bowling and billiard equipment, cable and satellite communication equipment, electronic components used in audio and video equipment, closed-circuit TV equipment and musical instruments.

These applications require implementation of PVDF in the molten state, like for example extrusion, and film injection or extrusion by film blowing techniques, or flat. During these implementations, the temperatures typically used are between 190 and 260° C., with residence times in the equipment that can vary from several tens of seconds (typically 30 seconds) up to several minutes, a time of 10 minutes, or even 15 minutes, is not unusual. This can lead to a thermal breakdown of the fluoridated polymer with, as a visible consequence, yellowing thereof, seen by a high yellowing index, for example over 15 in plate YI 230° C., 10 minutes. This phenomenon is related to the presence of impurities in the fluoridated polymer, in particular mercury and arsenic residues, which contaminate the raw materials, in particular ethylene of fossil origin used for synthesizing the VDF.

Since biosourced vinylidene difluoride is free of these impurities, any polymer containing it will advantageously have a higher degree of purity, which helps prevent the yellowing of the PVDF during high-temperature transformation.

Advantageously, the biosourced PVDF and/or biosourced fluoridated copolymers from the invention are used alone or in mixture with other polymers, where said biosourced fluoridated polymers represent from 5 to 100%, preferably from 5 to 70%, and preferably from 5 to 30% by mass.

The invention claimed is:

1. A biosourced vinylidene difluoride characterized in that the renewable carbon concentration is at least 1% by atom, as determined by the $^{14}$C concentration according to the NF EN 16640 standard.

2. The biosourced vinylidene difluoride according to claim 1, wherein the renewable carbon concentration is greater than 5.

3. A method for the preparation of biosourced vinylidene difluoride according to claim 1 comprising a step of providing biosourced ethylene or acetylene having a renewable carbon concentration of at least 1%, and the transformation into biosourced vinylidene difluoride by multistep synthesis wherein the first step of synthesis consists of the production of biosourced vinyl chloride monomer (VCM) from said biosourced ethylene or acetylene.

4. A method for the preparation of biosourced vinylidene difluoride according to claim 1 comprising a step of providing biosourced acetylene having a renewable carbon concentration of at least 1%, and the transformation into biosourced vinylidene difluoride by multistep synthesis wherein the first step of synthesis consists of the production of vinyl chloride monomer (VCM) biosourced from this biosourced acetylene.

5. The method according to claim 3 comprising the following sequence of steps:

Production of biosourced T112 (1,1,2-trichloroethane) by cold chlorination with Cl$_2$ from the biosourced VCM:

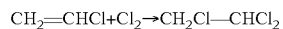

Production of biosourced T111 (1,1,1-trichloroethane) from biosourced T112:

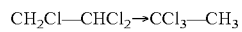

Production of biosourced 142 b (1,1,1-chlorodifluoroethane) from biosourced T111 and reaction with HF:

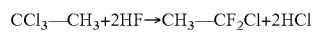

Production of biosourced vinylidene difluoride (VDF or CF$_2$=CH$_2$) from biosourced 142 b by thermal dehydrochlorination:

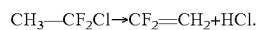

6. The method according to claim 3 comprising the following sequence of steps:

Production of biosourced T112 (1,1,2-trichloroethane) by cold chlorination with Cl$_2$ from the biosourced VCM:

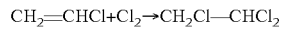

Production of biosourced CV2 (1,1-dichloroethene or CH$_2$=CCl$_2$) from biosourced T112 by dehydrochlorination by NaOH with production of brine:

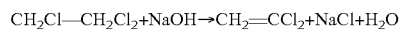

Production of biosourced 142 b (1,1,1-chlorodifluoroethane) from biosourced CV2 by fluoridation:

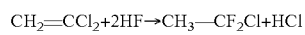

Production of biosourced vinylidene difluoride (VDF or CF$_2$=CH$_2$) from biosourced 142 b by thermal dehydrochlorination:

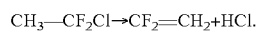

7. The method according to claim 3 comprising the following sequence of steps:

Production of biosourced D11 (1,1-dichloroethane) from the biosourced VCM by hydrochloridation:

$$CH_2=CHCl+HCl \rightarrow CHCl_2-CH_3$$

Production of biosourced T111 (1,1,1-trichloroethane) from biosourced D11 by chlorination:

$$CHCl_2-CH_3+Cl_2 \rightarrow CCl_3-CH_3+HCl$$

Production of biosourced 142 b (1,1,1-chlorodifluoroethane) from biosourced T111 and reaction with HF:

$$CCl_3-CH_3+2HF \rightarrow CH_3-CF_2Cl+2HCl$$

Production of biosourced vinylidene difluoride (VDF or $CF_2=CH_2$) from biosourced 142 b by thermal dehydrochlorination:

$$CH_3-CF_2Cl \rightarrow CF_2=CH_2+HCl.$$

8. A vinylidene difluoride homopolymer or copolymer comprising the biosourced vinylidene difluoride units according to claim 1.

9. The vinylidene difluoride homopolymer according to claim 8 consisting of the biosourced vinylidene difluoride units.

10. The fluoridated copolymers of claim 8 comprising the biosourced vinylidene difluoride units and one or more comonomer units compatible with vinylidene difluoride.

11. The fluoridated copolymers according to claim 10, wherein the comonomers of the vinylidene difluoride are selected from the group consisting of vinyl fluoride, tetrafluoroethylene, hexafluoropropylene, trifluoropropenes, hexafluoroisobutylene, perfluorobutylethylene, pentafluoropropenes perfluoroalkylvinylethers with general formula Rf—O—CF—CF$_2$, where Rf is an alkyl group.

12. An article of manufacture comprising the homopolymer or copolymer of claim 8, wherein the article is an electronic article.

13. The article of claim 12 wherein the vinylidene difluoride homopolymer or copolymer comprises from 5 to 100% by mass of total polymer in the article.

14. The article of claim 13 wherein the vinylidene difluoride homopolymer or copolymer comprises from 5 to 70% by mass of total polymer in the article.

* * * * *